United States Patent [19]

Verma

[11] Patent Number: 4,832,483
[45] Date of Patent: May 23, 1989

[54] METHOD OF USING RESONANCE RAMAN SPECTROSCOPY FOR DETECTION OF MALIGNANCY DISEASE

[75] Inventor: Surendra P. Verma, Sudbury, Mass.

[73] Assignee: New England Medical Center Hospitals, Inc., Boston, Mass.

[21] Appl. No.: 92,424

[22] Filed: Sep. 3, 1987

[51] Int. Cl.[4] ............................................. G01N 33/48
[52] U.S. Cl. ........................................ 356/39; 356/301
[58] Field of Search ................................. 356/39, 301

[56] References Cited

PUBLICATIONS

Sugarbaker et al., 1982, Diagnosis and Staging, In: de Vita, et al., eds., Cancer: Principles and Practice of Oncology, J. B. Lippinocott, Philadelphia, p. 248-254.
E. T. Fossel, et al., 1986, New England J. Med., vol. 315(22), pp. 1369-1376.
K. Larsson et al., 1974, Experientia, vol. 30, pp. 481-483.
A. J. Rein et al., 1976, Experientia, vol. 32, pp. 1352-1354.
G. Careri et al., 1970, Physics Letters, vol. 32A(7), pp. 495-496.
J. P. Biscar et al., 1972, Chemical Physics Letters, vol. 14(5), pp. 569-567.
J. P. Biscar et al., 1973, Polymer Letters Edition, vol. 11, pp. 725-729.
S. P. Verma et al., 1984, Biochem Biophys. Res. Commun., vol. 122(2), pp. 867-875.
S. P. Verma et al., 1985, Lipids, vol. 20(12), pp. 890-896.

Primary Examiner—Richard A. Rosenberger

[57] ABSTRACT

A method for determining the presence of malignancy disease in a subject person includes obtaining a test sample of blood plasma from the person, measuring intensities of Raman scattering from the plasma at frequencies in the frequency shift range between 1000 cm$^{-1}$ and 1600 cm$^{-1}$, and comparing the intensities to intensities of Raman scattering, at comparable frequencies, from normal human plasma.

11 Claims, 2 Drawing Sheets

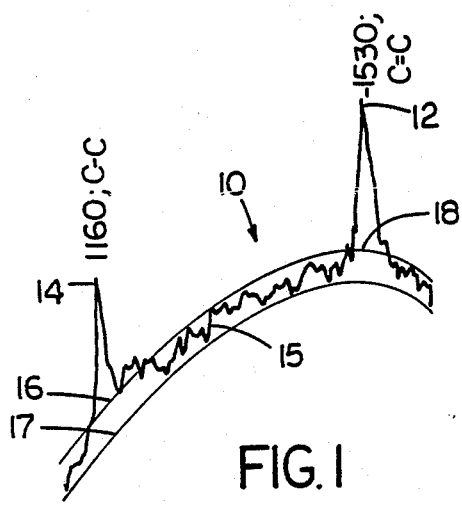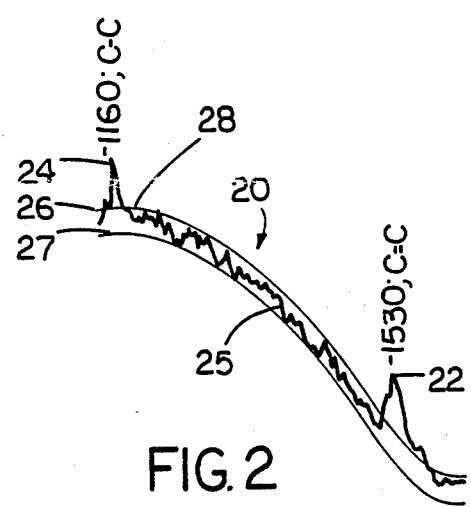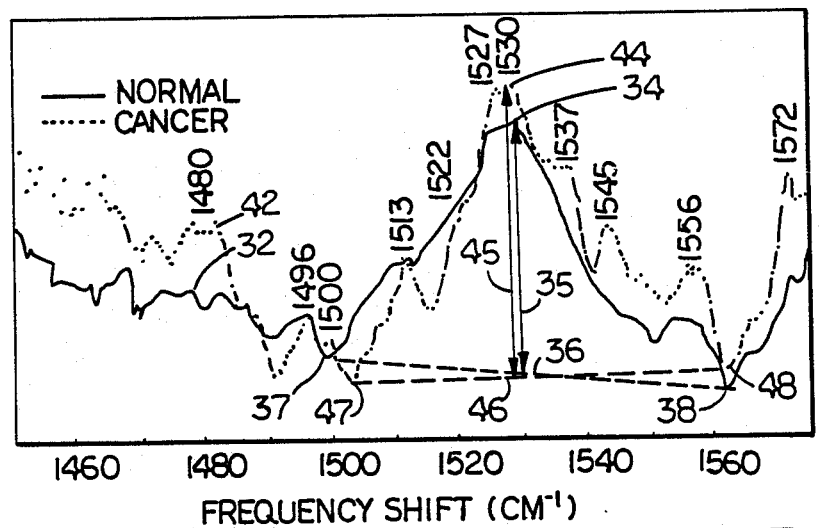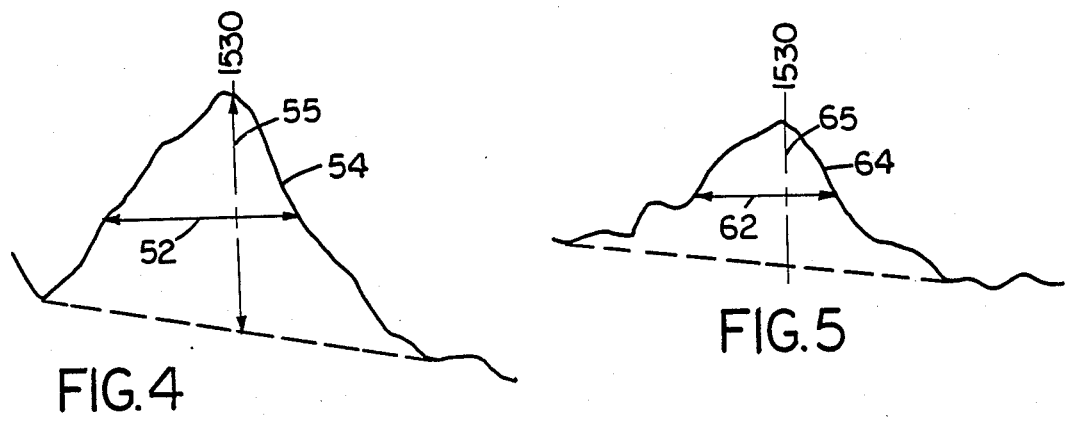

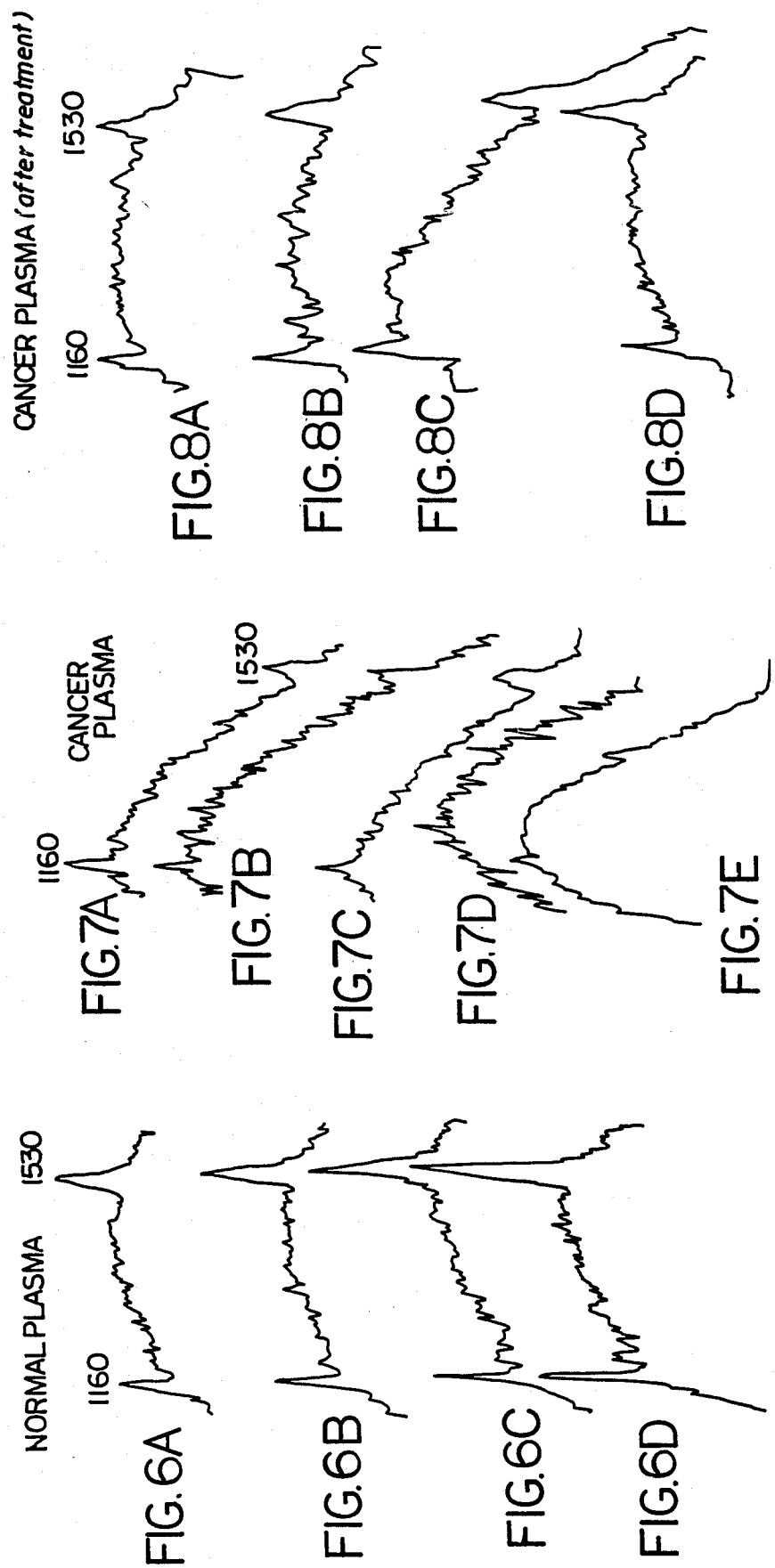

METHOD OF USING RESONANCE RAMAN SPECTROSCOPY FOR DETECTION OF MALIGNANCY DISEASE

Part of the work leading to this invention was made with U.S. Government funds. The U.S. Government has certain rights in this invention.

BACKGROUND OF THE INVENTION

This invention relates to diagnosis, staging, and monitoring of treatment of malignancy disease.

Tests proposed for the detection of malignancy using blood plasma include measurements of carcinoembryonic antigen, beta-human chorionic gonadotropin, and alpha-fetoprotein in serum (P. H. Sugarbaker et al., 1982, Diagnosis and Staging, In: de Vita, et al., eds., *Cancer: Principles and Practice of Oncology*, J. B. Lippincott, Philadelphia, pages 248-54), and water-suppressed proton nuclear magnetic resonance (NMR) spectroscopy of plasma (E. T. Fossel, et al., 1986, *New England J. Med.*, vol. 315(22), pages 1369-76).

K. Larsson et al., 1974, *Experientia*, vol. 30, pages 481-83, combined fluorescence and Raman spectra of plasma samples from healthy human subjects and from patients suffering from a variety of organic diseases including non-malignancy as well as malignanacy diseases. They noted that normal spectra have sharp Raman scattering bands at 1160 cm$^{-1}$, 1520 cm$^{-1}$, and 1010 cm$^{-1}$, broad unresolved Raman bands at about 3400 cm$^{-1}$, 3300 cm$^{-1}$, and 2900 cm$^{-1}$, and "[b]ackground fluorescence scattering characterized by moderate slope upwards in the range 1000 to 1600 cm$^{-1}$, and a horizontal niveau or a slight slope upwards in the range 1600 to 2800 cm$^{-1}$." They observed in samples from diseased individuals "strong changes in the background spectra due to ranges of the intrinsic fluorescence.

All patients with advanced carcinomas showed such a steep slope due to strong intrinsic fluorescence that the sharp Raman bands at 1160 and 1520 cm$^{-1}$ did not even show up in the spectra."

A. J. Rein et al., 1976, Experientia, vol. 32, pages 1352-54, produced resonance Raman spectra of human blood plasma over the frequency range 900 cm$^{-1}$ to 1600 cm$^{-1}$ and showed that the bands at 1517 cm$^{-1}$, 1157 cm$^{-1}$, and 1005 cm$^{-1}$ arise from carotenoids present in the plasma. Citing the work of K. Larsson et al., supra, they speculated that "[i]t may become possible, therefore, to both detect and investigate very specific disease states by examination of blood plasma using the rather unusual technique of resonance Raman spectroscopy."

G. Careri et al., 1970, *Physics Letters*, volume 32A(7), pages 495-496; J. P. Biscar et al., 1972, *Chemical Physics Letters*, volume 14(5), pages 569-7; and J. P. Biscar et al., 1973, *Polymer Letters Edition*, vol. 11, pages 725-29, studying the Raman behavior of purified proteins, demonstrated that some broad bands appearing in Raman spectrographs result from a "pseudo-Raman behavior", and not from intrinsic fluorescence, as generally assumed.

S. P. Verma et al., 1984, *Biochem. Biophys. Res. Commun.*, vol. 122(2), pages 867-875; and S. P. Verma et al., 1985, Lipids, vol. 20(12), pages 890-896, suggested that differences in the resonance Raman spectra of human plasma lipoprotein carotenoids near the 1530 cm$^{-1}$ band are caused by alterations in the lipid protein interactions of the carotenoid-carrying low-density lipoproteins (LDL). They assigned the 1160 cm$^{-1}$ band to C—C bond stretching vibrations, and the 1530 cm$^{-1}$ band to C=C bond stretching vibrations in the central part of the carotenoid chain.

SUMMARY OF THE INVENTION

In general, the invention features a method for determining the presence of malignancy disease in a subject person including obtaining a test sample of blood plasma from the person, measuring intensities of Raman scattering from the plasma at frequencies in the frequency shift range between 1000 cm$^{-1}$ and 1600 cm$^{-1}$, and comparing the intensities to intensities of Raman scattering, at comparable frequencies, from normal human plasma.

In preferred embodiments the method involves recording a plurality of intensities of the test sample and comparing them to a plurality of intensities, at comparable frequencies, of normal plasma.

In another aspect, the invention features a method for detecting the presence of malignancy disease in a subject person, including obtaining a test sample of blood plasma from the person, recording intensities of Raman scattering from the plasma at frequencies in the frequency shift range between 1000 cm$^{-1}$ and 1600 cm$^{-1}$, and determining from the recording a frequency at which the pseudo-Raman band reaches a maximum in the frequency shift range, whereby a presence of malignancy disease in the subject is indicated by a pseudo-Raman band maximum at a frequency in the frequency shift range between 1000 cm$^{-1}$ and 1350 cm$^{-1}$, and an absence of malignancy disease is indicated by a pseudo-Raman band maximum at a frequency in the frequency shift range between 1350 cm$^{-1}$ and 1600 cm$^{-1}$.

In prepared embodiments a presence of malignancy disease in the subject is indicated by a pseudo-Raman band maximum at a frequency in the frequency shift range between 1160 cm$^{-1}$ and 1250 cm$^{-1}$, and an absence of malignancy disease is indicated by a pseudo-Raman band maximum at a frequency in the frequency shift range between 1450 cm$^{-1}$ and 1530 cm$^{-1}$.

In another aspect, the invention features a method for detecting the presence of malignancy disease in a subject person, including obtaining a test sample of blood plasma from the person, recording intensities of Raman scattering from the plasma at frequencies in the frequency shift range between 1000 cm$^{-1}$ and 1600 cm$^{-1}$, determining from the recording the height, $I_{1530}$, of the 1530 cm$^{-1}$ peak at its maximum intensity, and the height of the 1160 cm$^{-1}$ peak at its maximum intensity, $I_{1160}$, whereby a presence of malignancy disease in the subject is indicated by a ratio $I_{1530}/I_{1160}$ in the range between 1.30 and 1.59, and an absence of malignancy disease is indicated by a ratio $I_{1530}/I_{1160}$ in the range between 1.00 and 1.20.

In another aspect, the invention features a method for detecting the presence of malignancy disease in a subject person, including obtaining a test sample of blood plasma from the person, recording intensities of Raman scattering from the plasma at frequencies in the frequency shift range between 1400 cm$^{-1}$ and 1600 cm$^{-1}$, and comparing the intensities to intensities of Raman scattering, at comparable frequencies, from normal human plasma.

In another aspect, the invention features a method for detecting the presence of malignancy disease in a subject person, including obtaining a test sample of blood plasma from the person, recording intensities of Raman scattering from the plasma at frequencies in the frequency shift range between 1500 cm$^{-1}$ and 1560 cm$^{-1}$, determining from the recording the shape of that portion of the 1530 cm$^{-1}$ band between 1500 cm$^{-1}$ and 1560 cm$^{-1}$, and measuring the half-height band width of the 1530 cm$^{-1}$ band, whereby a presence of malignancy disease in the subject is indicated by a 1530 cm$^{-1}$ half-height band width of 16.5±2.6 cm$^{-1}$, and an absence of malignancy disease is indicated by a half-height band width of 22±2.5 cm$^{-1}$.

In preferred embodiments the intensities of Raman scattering are recorded at regular intervals over at least a portion of said frequency shift range; the intervals are no greater than 100 cm$^{-1}$, and preferably no greater than 50 cm$^{-1}$; and the intervals are sufficiently small that together the recorded intensities form a substantially continuous spectrograph over a portion of the frequency shift range.

The method of the invention is noninvasive, requiring only a very small sample volume of blood plasma, and it can be carried out in less than 1 minute. The equipment used in carrying out the method can be operated by one having very little training.

The method of the invention can be used on a mass scale to screen human blood plasma for detection of a wide variety of malignancy diseases. The method can permit very early detection of cancer prior to clinical manifestation of disease. Also, this technique can be useful in monitoring the progress of therapy, as patients undergoing treatment, whose disease is in remission, have normal or nearly normal Raman spectra.

Other features and advantages of the invention will be apparent from the following description of the preferred embodiments, and from the claims.

DESCRIPTION OF THE PREFERRED EMBODIMENTS

We first briefly describe the drawings.
Drawings
FIG. 1 is a portion of a Raman/resonance Raman spectrum of plasma from a normal human subject.
FIG. 2 is a portion of a Raman/resonance Raman spectrum of plasma from a person having malignancy disease.
FIG. 3 is a portion of a higher resolution resonance Raman spectrum of plasma from a normal human subject and from a person having malignancy disease.
FIG. 4 is a portion of a higher-resolution resonance Raman spectrum of plasma from a normal human subject.
FIG. 5 is a portion of a higher-resolution resonance Raman spectrum of plasma from a person having malignancy disease.
FIGS. 6A-6D each is a portion of a Raman/resonance Raman spectrum of plasma from a normal human subject.
FIGS. 7A-7E each is a portion of a Raman/resonance Raman spectrum of plasma from a person having malignancy disease.
FIGS. 8A-8D each is a portion of a Raman/resonance Raman spectrum of plasma from a person undergoing treatment for malignancy disease.

GENERAL DESCRIPTION

I have discovered that in Raman/resonance Raman spectrographs of human blood plasma, the "pseudo-Raman" band in the frequency shift range between about 1120 cm$^{-1}$ and about 1590 cm$^{-1}$ has a characteristic configuration for normal individuals which is readily distinguishable from the various configurations of pseudo-Raman bands for individuals having any of a wide variety of malignancy diseases.

Moreover, I have discovered that the ratio of the heights of the resonance enhanced C=C and C—C carotenoid bands is less for normal subjects than for cancer patients; the shapes of the C=C bands adjacent the 1530 cm$^{-1}$ peak differ at least in the frequency shift range between about 1537 cm$^{-1}$ and about 1545 cm$^{-1}$; and the band width of the C=C band is greater for normal individuals than for those having malignancy diseases. As used herein, "1530 cm$^{-1}$ band" or "1530 cm$^{-1}$ peak" refers to the resonance enhanced signal near 1530 cm$^{-1}$, and "1160 cm$^{-1}$ band" or "1160 cm$^{-1}$ peak" refers to the resonance enhanced signal near 1160 cm$^{-1}$, without regard to whether the apex of the band is precisely at one of those frequencies.

For diagnosis either the configuration of the pseudo-Raman band or any of the characteristics of the carotenoid bands can be used as a criterion for comparison of the sample plasma spectrum to a normal spectrum; or any combination of these criteria can be used. As will be made clear in the description below, the method can detect the presence of malignancy disease in subjects who do not yet show clinical signs of cancer. Moreover, as will appear below, patients being treated for cancer whose disease is in remission yield spectra having characteristics approaching those of normal ones.

Plasma Samples

Fresh venous blood is collected from the subject, preferably in the morning hours after an overnight fast, using EDTA as an anticoagulant. A sample of 1 ml or less of blood suffices. Blood cells are separated from the plasma, preferably by centrifugation at 2000 rpm for 15 minutes using a tabletop centrifuge.

Raman/Resonance Raman Spectra

The Raman/resonance Raman spectrum is recorded using conventional Raman spectroscopic techniques. The spectra described and shown in the Figures herein were obtained by the following protocol, although it will be appreciated that spectra useful in the method of the invention can be obtained by procedures differing in particulars from that described here.

A plasma sample obtained, for example, as described above is transferred to a rotating cell, and its spectrum is recorded preferably as described in Verma et al., *Biochem. Biophys. Res. Commun.*, vol. 122, pages 867–75, using a triple monochromator scanning spectrometer (Dilor RTI/30; Lille, France), with four slits and three 1800 g/mm plane holographic gratings, interfaced to and driven by a computer (Tracor Northern TN-1710). The samples are excited at 488 nm with an Ar+ laser (Spectra Physics Model 164) at 50 mW power. Scanning from 800–1824 cm$^{-1}$ is carried out at an address advance of 1 cm$^{-1}$/channel, slits 200–400 microns (resolution 2 cm$^{-1}$), scanning speed 128 cm$^{-1}$/min, time constant 0.5 sec. A minimum of nine scans of each sample are accumulated in the computer memory before recording the spectrum on a strip chart recorder. The error in frequency of such measurements is less than 1.0 cm$^{-1}$.

Interpretation of the Spectra

By way of illustration, FIG. 1 shows an example of a portion of a Raman/resonance Raman spectrum 10, produced according to the procedures described above, of blood plasma from a human subject who is clinically free of malignancy disease. The spectrum 10 has an intense and sharp resonance enhanced band with a peak 12 at a frequency shift of about 1530 cm$^{-1}$, believed to be a carotenoid C=C stretching resonance peak, and a second intense and sharp resonance enhanced band with a peak 14 at a frequency shift of about 1160 cm$^{-1}$, believed to be a carotenoid C—C stretching resonance peak; and, between peaks 12 and 14, a broad pseudo-Raman band 15. As indicated by lines 16 and 17, superimposed on spectrum 10 for illustrative purposes, the pseudo-Raman band 15 for a cancer-free human subject is arcuate and generally slopes upward in the direction of higher frequency shift values (toward the right in FIG. 1), reaching a broad maximum 18 at a frequency shift between 1500 cm$^{-1}$ and 1550 cm$^{-1}$ and at an intensity (not scaled in the Figure) less than 2000 counts per second at 1500 cm$^{-1}$.

Again by way of illustration, FIG. 2 shows an example of a portion of a Raman/resonance Raman spectrum 20, similarly produced, of blood plasma from a human subject having active malignancy disease. Like normal spectrum 10, spectrum 20 also has an intense and sharp resonance enhanced band with a peak 22 at about 1530 cm$^{-1}$ and a second intense and sharp resonance enhanced band with a peak 24 at about 1160 cm$^{-1}$; and, between peaks 22 and 24, a broad pseudo-Raman band 25. As indicated by lines 26 and 27, superimposed on spectrum 20 for illustrative purposes, the pseudo-Raman band 25 for a human cancer patient is arcuate and generally slopes upward in the direction of lower frequency shift values (toward the left in FIG. 2), reaching a broad maximum 28 at a frequency shift between 1200 cm$^{-1}$ and 1250 cm$^{-1}$ and at an intensity (not scaled in the Figure) greater than 5000 counts per second at 1200 cm$^{-1}$.

Again by way of illustration, FIG. 3 shows a portion in the frequency shift range between 1450 cm$^{-1}$ and 1575 cm$^{-1}$ of a higher-resolution resonance Raman spectrum 32 from a normal human subject, superimposed for comparison on a portion in the same frequency shift range of a higher-resolution resonance Raman spectrum 42 from a human cancer patient. Spectrum 32 for normal plasma shows a main peak at about 1530 cm$^{-1}$ and weak shoulders at about 1513 cm$^{-1}$, 1527 cm$^{-1}$, and 1547 cm$^{-1}$. Spectrum 42 for plasma from a cancer patient differs in that it shows a distinct shoulder at about 1537 cm$^{-1}$, and a low peak at about 1545 cm$^{-1}$.

The ratio of the height of the C=C peak at about 1530 cm$^{-1}$ ["$I_{1530}$"] over the height of the C—C peak at about 1160 cm$^{-1}$ ["$I_{1160}$"] is greater in spectra from normal subjects than from cancer patients. The ratios are determined as follows. FIG. 3 shows the method of measuring peak height, using the peaks at about 1530 cm$^{-1}$ for illustration. The height of peak apex 34 is the vertical distance 35, in intensity units, from peak apex 34 to a straight line 36 drawn between the lowest point 37 on spectrum 32 at about 1500 cm$^{-1}$ and the lowest point 38 on spectrum 32 at about 1560 cm$^{-1}$; similarly, the height of peak apex 44 is the vertical distance 45, in intensity units, from peak apex 44 to a straight line 46 drawn between the lowest point 47 on spectrum 42 at about 1500 cm$^{-1}$ and the lowest point 48 on spectrum 42 at about 1560 cm$^{-1}$. For each spectrum, peak heights $I_{1530}$ and $I_{1160}$ are measured as described above, and the ratio [$I_{1530}/I_{1160}$] is determined by simple division. The value of this ratio for normal subjects varies from 1.00 to 1.20 and for cancer patients varies from 1.30 to 1.59.

The band width of the C=C band is less for persons having malignancy disease than for those who are free of malignancy. This is illustrated in the higher-resolution resonance Raman spectra, in the frequency-shift range between about 1495 cm$^{-1}$ and about 1560 cm$^{-1}$, shown in FIG. 4 (person free of malignancy) and FIG. 5 (person having malignancy disease). With reference to FIG. 4, the band width is the measure in frequency units of the horizontal distance 52 across the peak 54 at half the peak height 55, where peak height 55 is determined as described above. Similarly, with reference to FIG. 5, the band width is the measure in frequency units of the horizontal distance 62 across the peak 64 at half the peak height 65, where peak height 65 is determined as described above.

The band width of the C=C band for a person having malignancy disease generally falls within the range 16.5±2.5 cm$^{-1}$, and for a person free of malignancy it generally falls within the range 22±2.5 cm$^{-1}$. The band width of the C=C band for a person undergoing treatment for diagnosed malignancy disease is not significantly different from that for a person free of malignancy, where the disease is clinically in remission, generally falling in the range 20±2.5 cm$^{-1}$.

Demonstration

As a demonstration of the method of the invention, the plasma of 66 individual human subjects was screened using resonance Raman spectroscopy, without knowledge of their clinical status. The Raman spectra of plasmas obtained from different individuals varied in terms of the peak position, width and intensity of the pseudo-Raman band, and their shapes fell generally into the categories described above. After completion of the spectroscopic studies, the results were compared with the results of clinical tests on the individuals.

Their clinical status was as follows. Of the 66 subjects, 40 had no evidence of malignant disease at the time of or within 6 months after the spectroscopic studies, 22 had active malignant disease at the time of the spectroscopy, and 4 had a history of cancer but were free of disease at the time of the spectroscopy.

Spectra from Normal Subjects

In spectra of plasmas of normal individuals, of which 4 examples are shown in FIGS. 6A–6D, the pseudo-Raman band is very broad, having a broad peak between 1500 cm$^{-1}$ and 1550 cm$^{-1}$, and an intensity less than 2000 counts/sec at 1500 cm$^{-1}$. Rising from the pseudo-Raman band are intense and sharp plasma carotenoid peaks at 1160 cm$^{-1}$ and 1530 cm$^{-1}$.

The height ratios of the C=C and C=C bands fall in the range 1.00 to 1.20 in these spectra, and the C=C band widths fall in the range 22±2.5 cm$^{-1}$.

Spectra from Subjects Having Cancer

In spectra from plasmas of patients having active cancer, of which 5 examples are shown in FIGS. 7A–7E, the pseudo-Raman band is narrower, with a peak position between 1200 cm$^{-1}$ and 1250 cm$^{-1}$ at an intensity greater than 5000 counts/sec. The spectra in FIGS. 7A and 7C are from individuals who at the time of the spectroscopy had recently discovered cases of malignancy, and those in FIGS. 7D and 7E are from patients with advanced metastatic disease. The spectrum in FIG. 7B, whose pseudo-Raman band is characteristic of those from patients having active malignant disease, is from the plasma of a man who at the time of the spectroscopy showed no clinical signs of malignancy. Upon reexamination approximately six months later, the subject was clinically diagnosed as having adenocarcinoma of the prostate with progression of metastases.

The height ratios of the C=C and C—C bands fell in the range 1.30 to 1.59 in these spectra, and the C=C band width fell in the range $16.5\pm2.5$ cm$^{-1}$.

Spectra from Subjects Undergoing Treatment for Cancer

The spectra of plasmas from subjects who were being treated for cancer and who tested clinically negative for disease at the time of or within 6 months after the spectroscopy, of which 4 examples are shown in FIGS. 8A-8D, differ from those for subjects testing clinically positive for cancer who were not in treatment (FIGS. 7A-7E). The pseudo-Raman bands in these spectra generally are broader and have a lower intensity than those from cancer patients; the pseudo-Raman band maximum in FIG. 8C is at nearly the same frequency shift as that in spectra from cancer patients, but it is of considerably lower intensity.

The C=C band width for these spectra fell in the range $20\pm2.5$ cm$^{-1}$.

Other Embodiments

Other embodiments are within the following claims. For example, as will be apparent to one skilled in the art of Raman spectroscopy, any of a variety of lasers can be used; besides argon ion lasers, krypton ion lasers and argon-krypton ion lasers are preferred because they are in common use. The laser can be operated any of a number of excitation wavelengths, according to the practice of the particular user; commonly wavelengths between 457.9 and 647.1 nm are used, and preferably at 488 nm or 514.5 nm, as these lines produce high gain and output. The laser can be operated at as low as 1 mW, although the resulting signal will be generally less intense at lower powers; the power required to produce satisfactory results will differ for different samples, and in practice the power can be adjusted as required. Any number of scans of each sample can be made, and satisfactory results can be obtained from some samples after only a single scan. In practice the number of scans required can easily be varied according to experience: one or more scans can be accumulated in the computer memory and then recorded; if the results are not satisfactory then one or more further scans can be accumulated together with those already made and then all recorded; this accumulation of scans can be continued until the resulting spectrum is satisfactory.

A spectrum is satisfactory where the resonance enhanced peaks are discernible against the irregularity produced by background "noise", and where the shape of the pseudo-Raman band and the approximate frequency shift at which it reaches a maximum can be ascertained.

As will be appreciated by one skilled in the art of Raman Spectroscopy, any of a variety of machines for making measurements of Raman scattering can be used for the invention. For example, a double or even a single monochromator can be used, although the results generally have poorer resolution, and the triple monochromator is preferred where improved resolution is desired. Scanning can be manual or automated, and can be computer driven. Scanning parameters can be varied according to the quality of the particular sample, as is generally practiced in the art of Raman spectroscopy. Instead of a monochannel scanning approach as described above, in which a single channel scans the spectrum, reading at successive different wavelengths, a multichannel analysis can be employed for detecting the Raman signal. As is well-known, the multichannel approach detects the Raman signal at once over the entire desired frequency-shift spectrum via a number of channels reading at different wavelengths.

Moreover, although for illustrative purposes continuous spectra are shown herein, it can be advantageous to make measurements at greater frequency-shift intervals. For example, to determine the general shape of the pseudo-Raman band in the frequency-shift range between the carotenoic peaks, discrete measurements can be made at intervals of, for example, 50 cm$^{-1}$, and the resulting data points connected by a curve simply fit by eye. Or, discrete measurements can first be made at a lesser number of even greater intervals, the results inspected, and then if necessary further measurements made at smaller intervals within selected portions of the frequency shift range.

The measurements, whether they be at discrete frequency-shift intervals or in a continuous spectrum, can be "inspected" by the operator and recorded by hand, or any of the steps can be automated by use of electronic data processing means, without departing from the invention. For example, a computer suitably interfaced with the spectrometer can be programmed to determine the heights or the half-widths of the carotenoid bands, and can present to the operator either these data or some conclusion about the sample based on a comparison of the data.

The sample can be excited by any of a variety of sources, at any frequency within a range of frequencies, and at any power sufficient to produce adequate signals, as is will be recognized by one of ordinary skill in the art of Raman spectroscopy. For example, any laser can be used. Moreover, a light source that is itself non-monochromatic can be used, such as, for example, sunlight or a mercury-arc lamp, and an essentially monochromatic excitation beam can be selected from the source output and directed onto the sample by well-known techniques; but a laser is preferred because it produces a higher-intensity excitation beam with lower power requirements.

I claim:

1. A method for determining the presence of malignancy disease in a subject person, comprising
   obtaining a test sample of blood plasma from the person, and
   measuring intensities of Raman scattering from said plasma at frequencies in the frequency shift range between 1000 cm$^{-1}$ and 1600 cm$^{-1}$,
   a substantial difference between said intensities and intensities of Raman scattering, at comparable frequencies, from normal human plasma indicating a presence of malignancy disease in the person.

2. The method of claim 1 wherein said method involves recording a plurality of said intensities of said test sample and comparing said plurality of recorded intensities to a plurality of intensities, at comparable frequencies, of said normal plasma.

3. A method for detecting the presence of malignancy disease in a subject person, comprising obtaining a test sample of blood plasma from the person, recording intensities of Raman scattering from said plasma at frequencies in the frequency shift range between 1000 cm$^{-1}$ and 1600 cm$^{-1}$, and determining from said recording a frequency at which the pseudo-Raman band reaches a maximum in said frequency shift range, a said pseudo-Raman band maximum at a frequency in the frequency shift range between 1000 cm$^{-1}$ and 1350 cm$^{-1}$ indicating a presence of malignancy disease in the person, and a said pseudo-Raman band maximum at a frequency in the frequency shift range between 1350 cm$^{-1}$ and 1600 cm$^{-1}$ indicating an absence of malignancy disease in the person.

4. The method of claim 3, a said pseudo-Raman band maximum at a frequency in the frequency shift range between 1160 cm$^{-1}$ and 1250 cm$^{-1}$ indicating a presence of malignancy disease in the person, and a said pseudo-Raman band maximum at a frequency in the frequency shift range between 1450 cm$^{-1}$ and 1530 cm$^{-1}$ indicating an absence of malignancy disease in the person.

5. A method for detecting the presence of malignancy disease in a subject person, comprising obtaining a test sample of blood plasma from the person, recording intensities of Raman scattering from said plasma at frequencies in the frequency shift range between 1000 cm$^{-1}$ and 1600 cm$^{-1}$, determining from said recording the height, $I_{1530}$, of the 1530 cm$^{-1}$ peak at its maximum intensity, and determining from said recording the height of the 1160 cm$^{-1}$ peak at its maximum intensity, $I_{1160}$, a said ratio $I_{1530}/I_{1160}$ in the range between 1.30 and 1.59 indicating a presence of malignancy disease in the person, and a said ratio $I_{1530}/I_{1160}$ in the range between 1.00 and 1.20 indicating an absence of malignancy disease in the person.

6. A method for detecting the presence of malignancy disease in a subject person, comprising obtaining a test sample of blood plasma from the person, and recording intensities of Raman scattering from said plasma at frequencies in the frequency shift range between 1400 cm$^{-1}$ and 1600 cm$^{-1}$, a substantial difference between said intensities and intensities of Raman scattering, at comparable frequencies, from normal human plasma indicating a presence of malignancy disease in the person.

7. A method for detecting the presence of malignancy disease in a subject person, comprising obtaining a test sample of blood plasma from the person, recording intensities of Raman scattering from said plasma at frequencies in the frequency shift range between 1500 cm$^{-1}$ and 1560 cm$^{-1}$, determining from said recording the shape of that portion of the 1530 cm$^{-1}$ band between 1500 cm$^{-1}$ and 1560 cm$^{-1}$, and measuring the half-height band width of said 1530 cm$^{-1}$ band, a said half-height band width of $16.5 \pm 2.6$ cm$^{-1}$ indicating a presence of malignancy disease in the person, and a said half-height band width of $22 \pm 2.5$ cm$^{-1}$ indicating an absence of malignancy disease in the person.

8. The method of claim 3, 5, 6, or 7 wherein said intensities of Raman scattering are recorded at regular intervals over at least a portion of said frequency shift range.

9. The method of claim 8 wherein said intervals are no greater than 100 cm$^{-1}$.

10. The method of claim 8 wherein said intervals are no greater than 50 cm$^{-1}$.

11. The method of claim 8 wherein said intervals are sufficiently small that together said recorded intensities comprise a substantially continuous spectrograph over said portion of said frequency shift range.

* * * * *